US008956631B2

(12) United States Patent
Giroud et al.

(10) Patent No.: US 8,956,631 B2
(45) Date of Patent: *Feb. 17, 2015

(54) COSMETIC COMPOSITIONS COMPRISING AT LEAST ONE NON-IONIC SURFACTANT AND AT LEAST ONE VINYLAMIDE/VINYLAMINE COPOLYMER AND METHODS OF USE THEREOF

(75) Inventors: Franck Giroud, Chamoux sur Gelon (FR); Paul Laurence, Saint leu la Foret (FR); Henri Samain, Bievres (FR)

(73) Assignee: L'Oreal, Paris (FR)

( * ) Notice: Subject to any disclaimer, the term of this patent is extended or adjusted under 35 U.S.C. 154(b) by 1503 days.

This patent is subject to a terminal disclaimer.

(21) Appl. No.: 12/078,584

(22) Filed: Apr. 2, 2008

(65) Prior Publication Data

US 2008/0260666 A1     Oct. 23, 2008

Related U.S. Application Data

(60) Provisional application No. 60/907,567, filed on Apr. 9, 2007.

(30) Foreign Application Priority Data

Apr. 2, 2007  (FR) ..................... 07 54210

(51) Int. Cl.
| | | |
|---|---|---|
| A61K 8/02 | (2006.01) |
| A61K 8/81 | (2006.01) |
| A61K 8/39 | (2006.01) |
| A61K 8/60 | (2006.01) |
| A61Q 1/14 | (2006.01) |
| A61Q 5/02 | (2006.01) |
| A61Q 5/06 | (2006.01) |
| A61Q 5/12 | (2006.01) |

(52) U.S. Cl.
CPC . *A61K 8/817* (2013.01); *A61K 8/39* (2013.01); *A61K 8/604* (2013.01); *A61Q 1/14* (2013.01); *A61Q 5/02* (2013.01); *A61Q 5/06* (2013.01); *A61Q 5/12* (2013.01)
USPC ........................................ 424/401

(58) Field of Classification Search
USPC ........................................ 424/401
See application file for complete search history.

(56) References Cited

U.S. PATENT DOCUMENTS

| | | | |
|---|---|---|---|
| 2,528,378 A | 10/1950 | Mannheimer | |
| 2,781,354 A | 2/1957 | Mannheimer | |
| 4,342,744 A | 8/1982 | Arai et al. | |
| 4,713,236 A | 12/1987 | Hoover et al. | |
| 4,764,363 A | 8/1988 | Bolich, Jr. | |
| 5,324,506 A * | 6/1994 | Calvo et al. ..................... 424/63 |
| 5,632,977 A * | 5/1997 | Chandran et al. ........... 424/70.17 |
| 5,753,759 A * | 5/1998 | Hartmann et al. ............. 525/218 |
| 6,630,133 B1 | 10/2003 | Dupuis | |
| 7,919,106 B2 * | 4/2011 | Giroud et al. ................. 424/401 |
| 2003/0199642 A1 | 10/2003 | Schneider et al. | |
| 2005/0129646 A1 | 6/2005 | Vic et al. | |
| 2005/0245684 A1 | 11/2005 | Daniel et al. | |
| 2005/0276777 A1 * | 12/2005 | Lalleman et al. .......... 424/70.13 |
| 2006/0286057 A1 * | 12/2006 | Cannell et al. ............. 424/70.12 |
| 2007/0110690 A1 | 5/2007 | Nguyen et al. | |
| 2008/0182773 A1 | 7/2008 | Gauweiler et al. | |
| 2009/0202465 A1 | 8/2009 | Mougin et al. | |
| 2011/0186070 A1 * | 8/2011 | Verboom ...................... 132/203 |

FOREIGN PATENT DOCUMENTS

| | | |
|---|---|---|
| DE | 195 40 853 A1 | 5/1997 |
| DE | 10 2005 014 293 A1 | 9/2006 |
| EP | 1 779 894 | 5/2007 |
| JP | 2002-255756 | 9/2002 |
| WO | WO 96/03969 A1 | 2/1996 |
| WO | WO 02/15854 | 2/2002 |
| WO | WO 2007/003784 A1 | 1/2007 |

OTHER PUBLICATIONS

JP 2002-255756, Machine Translation, retrieved online on Jun. 21, 2011, p. 1-9.*

(Continued)

*Primary Examiner* — Blessing M Fubara
*Assistant Examiner* — Jennifer A Berrios
(74) *Attorney, Agent, or Firm* — The Marbury Law Group, PLLC

(57) ABSTRACT

Disclosed herein are cosmetic compositions comprising:
  at least one non-ionic surfactant chosen from alkylpolyglycosides and mono- and polyglycerolated surfactants, and
  at least one vinylformamide/vinylamine copolymer comprising:
from 10 to 90 mol % of units of following formula A:

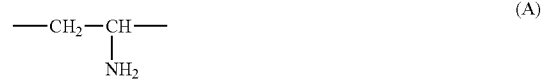

(A)

and from 90 to 10 mol % of units of following formula B:

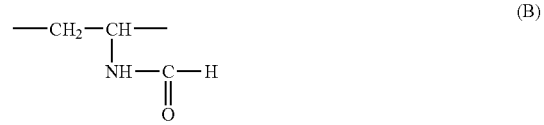

(B)

and a method for treating keratinous substances using said composition.

22 Claims, No Drawings

(56) References Cited

OTHER PUBLICATIONS

French Search Report for FR 0754210, dated Nov. 13, 2007.
English language abstract of DE 195 40 853 A1, May 7, 1997.
English language abstract of DE 10 2005 014 293 A1, Sep. 28, 2006.
Copending Application No. 12/362,848, filed Jan. 30, 2009.
English language Abstract of EP 1 779 894, dated May 2, 2007.
English language Abstract of JP 2002-255756, dated Sep. 11, 2002.
French Search Report for FR 08/50607, dated Sep. 24, 2008.
Office Action mailed Oct. 5, 2011, in co-pending U.S. Appl. No. 12/362,848.

* cited by examiner

COSMETIC COMPOSITIONS COMPRISING AT LEAST ONE NON-IONIC SURFACTANT AND AT LEAST ONE VINYLAMIDE/VINYLAMINE COPOLYMER AND METHODS OF USE THEREOF

This application claims benefit of U.S. Provisional Application No. 60/907,567, filed Apr. 9, 2007, the contents of which are incorporated herein by reference. This application also claims benefit of priority under 35 U.S.C. §119 to French Patent Application No. FR 0754210, filed Apr. 2, 2007, the contents of which are also incorporated herein by reference.

The present disclosure relates to compositions comprising at least one specific non-ionic surfactant and at least one vinylamide/vinylamine copolymer.

It is known practice in the cosmetics field such as the hair field, to employ polymers in leave-in products, for example for contributing hold to the hair or creating a style.

Use is also made, in the field of "rinse-out" hair compositions, such as shampoos or conditioners, of water-soluble synthetic cationic polymers which are known for contributing a good cosmetic quality to the hair; however, these polymers may not contribute to any effect in shaping the hair. Cationic natural derived polymers, such as modified guar gums, are also known to contribute an acceptable cosmetic quality, but may also not contribute to sufficient styling of the hair.

Disclosed herein are cosmetic compositions comprising polymers capable of contributing a true styling effect while having good cosmetic properties.

International Patent Application No. WO 96/03969 describes hair fixing compositions comprising polyvinylformamides. However, these polymers may not make it possible to obtain a lasting hold.

U.S. Patent Application Publication No. 2006/0286057, International Application No. WO 2007/03784 and German Patent Application No. DE10 2005 014293 disclose compositions comprising vinylamine/vinylamide copolymers but not comprising a non-ionic surfactant.

The present inventors have discovered, surprisingly, that the combination of at least one vinylformamide/vinylamine copolymer as defined below and of at least one non-ionic surfactant chosen from alkylpolyglycosides and/or mono- and polyglycerolated surfactants, for the preparation of compositions, such as rinse-out compositions, can have true properties of lasting form retention and good cosmetic properties.

Thus, one aspect of the present disclosure is a cosmetic composition comprising, in a cosmetically acceptable medium:

at least one non-ionic surfactant chosen from alkylpolyglycosides, mono- and polyglycerolated surfactants, and at least one vinylformamide/vinylamine copolymer comprising:

from 10 to 90 mol % of units of formula A:

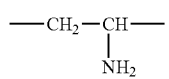

and from 90 to 10 mol % of units of formula B:

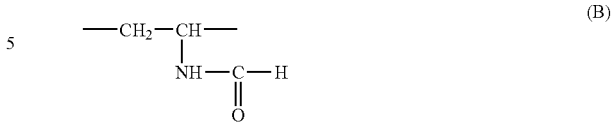

Surprisingly, the compositions disclosed herein, may have beneficial cosmetic properties, for example when applied in a formulation of shampoo type; this is because it has been found that the hair exhibits good cosmetic properties, such as disentangling, smoothing, softness and shine, the compositions may make it possible to obtain, once the hair is dried, a shaping of the hair and a hold that is beneficial.

Another aspect of the present disclosure is the cosmetic use of the above compositions for cleaning and/or removing makeup from and/or conditioning keratinous substances, such as the hair and skin. Yet another aspect of the present disclosure is the use of the composition as disclosed herein as a shampoo for keratinous substances.

Non-Ionic Surfactant(s):

According to at least one embodiment of the present disclosure, the at least one non-ionic surfactant is chosen from alkylpolyglycosides of formula (I):

wherein $R_1$ is chosen from linear and branched alkyl and/or alkenyl radicals comprising from 8 to 24 carbon atoms and alkylphenyl radicals, the linear or branched alkyl radical of which comprises from 8 to 24 carbon atoms, $R_2$ is an alkylene radical comprising from 2 to 4 carbon atoms, G is a sugar unit comprising 5 or 6 carbon atoms, t is a value ranging from 0 to 10, such as from 0 to 4, and v is a value ranging from 1 to 15.

In at least one embodiment, the alkylpolyglycosides are compounds of formula (I) wherein $R_1$ is chosen from saturated and unsaturated and linear and branched alkyl radicals comprising from 8 to 18 carbon atoms, t is a value ranging from 0 to 3, for example 0, and G is chosen from glucose, fructose and galactose, for instance, glucose. The degree of polymerization, i.e. the value of v in the formula (I), can range from 1 to 15, such as from 1 to 4. The mean degree of polymerization can range, for example from 1 to 2 and further, for example from 1.1 to 1.5.

The glycoside bonds between the sugar units are of 1-6 or 1-4 type, for instance, 1-4 type.

Examples of compounds of formula (I) include, but are not limited to the products sold by Cognis under the names PLANTAREN® (600 CS/U, 1200 and 2000) or PLANTACARE® (818, 1200 and 2000). Non-limiting mention may also be made of the products sold, for example, by Seppic under the names TRITON CG 110 (or ORAMIX CG 110) and TRITON CG 312 (or ORAMIX® NS 10), the products sold, for instance, by BASF under the name LUTENSOL GD 70 or the products sold, for example, by Chem Y under the name AG10 LK.

Another useful example of the compounds of formula (I) are the C8/C16 alkyl poly-1,4-glucoside in 53% aqueous solution sold by Cognis under the name PLANTACARE® 818 UP.

According to at least one embodiment of the present disclosure, the at least one non-ionic surfactant chosen from mono- or polyglycerolated surfactants comprises, on average, from 1 to 30 glycerol groups, for example, from 1 to 10 glycerol groups and further for example, 1.5 to 5 glycerol groups.

In at least one embodiment, the monoglycerolated or polyglycerolated surfactants are chosen from:

A) compounds chosen from those of formulae: $RO[CH_2CH(CH_2OH)O]_mH$, $RO[CH_2CH(OH)CH_2O]_mH$, and $RO[CH(CH_2OH)CH_2O]_mH$; wherein R is chosen from saturated and unsaturated and linear and branched hydrocarbon radicals comprising from 8 to 40 carbon atoms, for example, from 10 to 30 carbon atoms; and m is a number ranging from 1 to 30, for instance, from 1 to 10, such as from 1.5 to 5.

R can optionally comprise heteroatoms, such as oxygen and nitrogen. For example, R can optionally comprise at least one hydroxyl group and/or at least one ether group and/or at least one amide group.

In one embodiment, R is chosen from optionally mono- or polyhydroxylated $C_{10}$-$C_{20}$ alkyl radicals and optionally mono- or polyhydroxylated $C_{10}$-$C_{20}$ alkenyl radicals.

Non-limiting mention may be made of the polyglycerolated (3.5 mol) hydroxylauryl ether sold, for instance, under the name CHIMEXANE® NF by Chimex.

The at least one non-ionic surfactant chosen from alkylpolyglycosides and mono- or polyglycerolated surfactants can be chosen from, in at least one embodiment, alkylpolyglycosides such as ($C_6$-$C_{24}$)alkylpolyglycosides and ($C_8$-$C_{16}$) alkylpolyglycosides.

The at least one non-ionic surfactant, chosen from alkylpolyglycosides and mono- or polyglycerolated surfactants, is present in an amount ranging from 0.1 to 40% by weight, relative to the total weight of the composition, such as ranging from 1 to 30% by weight, for example from 5 to 25% by weight, and further for example, from 8 to 20% by weight.

Vinylformamide/Vinylamine Copolymer

According to at least one embodiment of the present disclosure, the at least one vinylamine/vinylamide copolymer may comprise from 10 to 60 mol % of units of formula A, such as from 20 to 40 mol %.

In another embodiment, the at least one vinylamine/vinylamide copolymer may comprise from 30 to 90 mol % of unit of formula B, such as from 60 to 80 mol %.

The copolymers disclosed herein can be obtained by partial hydrolysis of polyvinylformamide. The hydrolysis can be carried out in an acidic or basic medium.

The at least one vinylamine/vinylamide copolymer as disclosed herein, can optionally comprise at least one additional monomer unit. When present in the at least one vinylamine/vinylamide copolymer, the at least one additional monomer unit can be present in an amount less than 20 mol % of the copolymer.

According to at least one embodiment, the at least one vinylamine/vinylamide copolymer is composed solely of units A and of units B.

The weight-average molecular weight, measured by light diffraction, can vary from 10,000 to 30,000,000 g/mol, for example from 40,000 to 1,000,000 g/mol, such as from 100,000 to 500,000 g/mol.

The cationic charge density of the at least one vinylamine/vinylamide copolymer at pH 5 can vary from 2 meq/g to 20 meq/g, for instance from 2.5 to 15 meq/g, such as from 3.5 to 10 meq/g.

Mention may be made among vinylamine/vinylamide copolymers of the present disclosure, by way of non-limiting example, of LUPAMIN 9030 and 9010 provided by BASF.

The at least one vinylamine/vinylamide copolymer as disclosed herein, is present in an amount ranging from 0.01 to 20% by weight, relative to the total weight of the composition, for example, from 0.05 to 10% by weight, such as from 0.1 to 5% by weight.

The compositions, in accordance with the present disclosure, can additionally comprise at least one additional surfactant, such as anionic, amphoteric or zwitterionic surfactants and mixtures thereof. The compositions, as disclosed herein, can also comprise non-ionic surfactants other than the non-ionic surfactants chosen from alkylpolyglycosides and mono- or polyglycerolated surfactants.

Examples of suitable amphoteric or zwitterionic surfactants, include, but are not limited to aliphatic secondary or tertiary amine derivatives wherein the aliphatic radical is a linear or branched chain comprising from 8 to 18 carbon atoms and comprising at least one water-solubilizing anionic group, for example carboxylate, sulfonate, sulfate, phosphate and phosphonate groups. Non-limiting mention may also be made of ($C_8$-$C_{20}$)alkyl betaines, sulfobetaines, ($C_8$-$C_{20}$)alkyl amido($C_1$-$C_6$)alkyl betaines and ($C_8$-$C_{20}$)alkyl amido($C_1$-$C_6$)alkyl sulfobetaines.

Examples of amine derivatives include, but are not limited to the products sold under the MIRANOL name, as described in U.S. Pat. Nos. 2,528,378 and 2,781,354, and categorized in the CTFA dictionary, 3rd Edition, 1982, under the names Amphocarboxyglycinates and Amphocarboxypropionates with the respective structures:

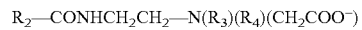

wherein: $R_2$ is chosen from alkyl radicals of an acid $R_2$—COOH present in hydrolysed coconut oil and heptyl, nonyl and undecyl radicals, $R_3$ is a β-hydroxyethyl group and $R_4$ is a carboxymethyl group; and

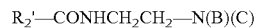

wherein:
(B) is —$CH_2CH_2OX'$; (C) is —$(CH_2)_z$—Y', with z=1 or 2,
X' is chosen from —$CH_2CH_2$—COOH and hydrogen atoms,
Y' is chosen from —COOH and —$CH_2$—CHOH—$SO_3H$ radicals, and
$R_2$' is chosen from alkyl radicals of an acid $R_2$'—COOH present in hydrolysed linseed oil and coconut oil, alkyl radicals, for example, $C_7$, $C_9$, $C_{11}$, $C_{13}$ alkyl radicals, and $C_{17}$ alkyl radicals and their iso form, and unsaturated $C_{17}$ radicals.

These compounds are categorized in the CTFA dictionary, 5th Edition, 1993, under the names Disodium Cocoamphodiacetate, Disodium Lauroamphodiacetate, Disodium Caprylamphodiacetate, Disodium Caproamphodiacetate, Disodium Cocoamphodipropionate, Disodium Lauroamphodipropionate, Disodium Caprylamphodipropionate, Disodium Caproamphodipropionate, Lauroamphodipropionic Acid, Cocoamphodipropionic Acid and Disodium Cocoamphocarboxy Ethyl Hydroxypropyl Sulfonate.

Non-limiting mention may be made of the cocoamphodiacetate sold, for example under the trade name MIRANOL® C2M Concentrate by Rhodia Chimie.

The composition, according to the present disclosure, can also comprise at least one anionic surfactant, for example carboxylic anionic surfactants.

Suitable examples of anionic surfactants include, but are not limited to salts, for example alkaline salts, sodium salts, ammonium salts, amine salts, aminoalcohol salts and magnesium salts; alkyl sulfates; alkyl ether sulfates; alkylamido ethersulfates; alkylaryl polyether sulfates; monoglyceride sulfates; alkylsulfonates; alkyl phosphates; alkylamidesulfonates; alkylarylsulfonates; α-olefinsulfonates; paraffinsulfonates; alkyl sulfosuccinates; alkyl ether sulfosuccinates; alkylamide sulfosuccinates; alkyl sulfosuccinamates; alkyl sulfoacetates; alkyl ether phosphates; acylsarcosinates; acylisethionates, N-acyltaurates, and mixtures thereof; the alkyl or acyl radical of all these different compounds comprising, in at least one embodiment, from 12 to 20 carbon atoms and the aryl radical, in at least one embodiment, chosen from phenyl and benzyl groups.

Other useful anionic surfactants include, but are not limited to carboxylic anionic surfactants, such as alkyl-D-galactosideuronic acids and the salts thereof, and polyoxyalkylenated ether carboxylic acids and the salts thereof, such as those comprising from 2 to 50 ethylene oxide groups, and the mixtures thereof.

The anionic surfactants of the polyoxyalkylenated ether carboxylic acid or salt thereof type are, for example, those of formula (II):

$$R_1—(OC_2H_4)_n—OCH_2COOA \quad (II)$$

wherein:

$R_1$ is chosen from alkyl, alkylamido and alkaryl groups and n is an integer or a decimal number (mean value) ranging from 2 to 24, for instance, from 3 to 10, the alkyl radical comprising approximately 6 to 20 carbon atoms and in at least one embodiment, the aryl is phenyl, A is chosen from H, ammonium, Na, K, Li, Mg and monoethanolamine and triethanolamine residues. According to at least one embodiment, mixtures of compounds of formula (II), for example, mixtures wherein the $R_1$ groups are different, may be used.

Non-limiting examples of compounds of formula (II) are sold, for example, by Chem Y under the AKYPO names (NP40, NP70, OP40, OP80, RLM25, RLM38, RLMQ 38 NV, RLM 45, RLM 45 NV, RLM 100, RLM 100 NV, RO 20, RO 90, RCS 60, RS 60, RS 100, RO 50) or by Sandoz under the SANDOPAN names (DTC Acid, DTC).

In at least one embodiment of the present disclosure, polyoxyalkylenated alkyl ether carboxylic acids, such as lauryl ether carboxylic acid (4.5 OE), for example sold under the name AKYPO RLM 45 CA by Kao, are used.

According to at least one embodiment of the present disclosure, the at least one anionic surfactant, in combination with the carboxylic anionic surfactants, is chosen from sodium and/or ammonium lauryl ether sulfate, and sodium and/or ammonium lauryl sulfate.

When present in the composition, the at least one additional surfactant is present in an amount ranging from 0.1 to 20% by weight, relative to the total weight of the composition, for example from 1 to 15% by weight, such as from 1.5 to 10% by weight.

According to at least one embodiment, the compositions can comprise a total concentration of surfactants ranging from 4 to 50% by weight, relative to the total weight of the composition, for example from 8 to 30% by weight.

The composition may further comprise at least one additional conditioning agent other than the at least one vinylamine/vinylamide copolymer.

When the composition comprises at least one additional conditioning agent, it can be chosen from, by way of non-limiting example: synthetic oils, such as poly-α-olefins, fluorinated oils, fluorinated waxes, fluorinated gums, non-fluorinated waxes, fatty esters of carboxylic acids, cationic polymers, silicones, mineral, vegetable and animal oils, ceramides, pseudoceramides and mixtures thereof.

According to one embodiment, the at least one additional conditioning agent is chosen from cationic polymers other than the at least one vinylamine/vinylamide copolymer, and silicones. In another embodiment, the at least one additional conditioning agent is chosen from silicones, such as non-volatile silicones.

When present in the composition, the at least one additional conditioning agent is present in an amount ranging from 0.001% to 25% by weight, relative to the total weight of the composition, for example, from 0.005% to 10% by weight and further for example, from 0.01% to 5% by weight.

When present in the composition, the at least one cationic polymer is present in an amount ranging from 0.01 to 20% by weight, relative to the total weight of the composition, for example from 0.05 to 10% by weight, and further for example from 0.1 to 5% by weight.

Non-limiting mention may be made, as suitable silicones, of volatile or non-volatile, cyclic or acyclic, branched or unbranched and organomodified or non-organomodified silicones.

The at least one silicone, which can be used in accordance with the present disclosure, may be soluble or insoluble in the composition, for instance, polyorganosiloxanes which are insoluble in the composition disclosed herein; they can be provided in the form of oils, waxes, resins or gums.

In at least one embodiment, the at least one silicone is chosen from non-ionic polydimethylsiloxanes comprising trimethylsilyl end groups and dimethylsilanol end groups (Dimethicone or dimethiconol according to the INCI nomenclature).

According to the present disclosure, the at least one silicone can be used as-is or in the form of solutions, dispersions, emulsions, nanoemulsions or microemulsions.

The at least one silicone, which can be used alone or as a mixture, can be present in an amount ranging from 0.01 to 20% by weight, relative to the total weight of the composition, for example, from 0.1 to 5% by weight.

The composition, according to the present disclosure, can also further comprise at least one adjuvant commonly used in cosmetics, such as vitamins, fragrances, pearlescent agents, thickeners, polymers other than the vinylformamide/vinylamine copolymers disclosed herein, gelling agents, trace elements, softeners, sequestering agents, basifying or acidifying agents, preservatives, sunscreens, antioxidants, agents for combating hair loss, antidandruff agents, agents for combating fats, agents for combating free radicals, and mixtures thereof. Of course, a person skilled in the art will take care to choose this or these optional additional compounds and/or their amounts so that the beneficial properties of the composition according to the present disclosure are not, or not substantially, detrimentally affected by the envisaged addition.

The pH of the composition as disclosed herein ranges from 2 to 11, for example, from 3 to 10, and further for example, from 5 to 8.

The medium of the composition, according to the present disclosure, may be chosen from water, hydrophilic organic solvents, polyols and glycol ethers, and mixtures thereof.

The composition, according to the present disclosure, can further comprise at least one propellant. The propellant is chosen, for example, from the compressed or liquefied gases commonly employed in the preparation of aerosol compositions, and mixtures thereof. Examples of gases include, but are not limited to air, carbon dioxide and nitrogen which is compressed, and also a soluble gas, such as dimethyl ether, halogenated, for example, fluorinated, or non-halogenated hydrocarbons, and mixtures thereof.

The hair compositions may be in various forms such as shampoos, gels, hair setting lotions, blow drying lotions or fixing and styling compositions, such as lacquers or sprays. The lotions can be packaged, for example, in vaporizers or pump-action sprays or in aerosol containers, in order to ensure application of the composition in the vaporized form or in the foam form.

According to at least one embodiment, the compositions can be used for washing and treating keratinous substances, such as the hair, skin, eyelashes, eyebrows, nails, lips or scalp, for example, the hair.

The composition as disclosed herein can be employed as a detergent composition, such as shampoos, shower gels and foam baths. When employed as a detergent composition, the composition may comprise at least one anionic and/or non-ionic detergent surfactant in an amount of at least 4% by weight, relative to the total weight of the composition.

A further aspect of the present disclosure is a method for the treatment of keratinous substances, such as the skin or hair, comprising applying to the keratinous substances, a cosmetic composition as defined above and in then optionally rinsing with water.

Thus the method, according to the present disclosure, makes it possible to retain the form of the hairstyle or to treat, care for, wash or remove makeup from the skin, hair or any other keratinous substance.

In at least one embodiment, the compositions of the present disclosure can be provided in the form of a rinse-out or leave-in conditioner or also in the form of a rinse-out composition to be applied before or after any hair treatment, for example, a dyeing operation, a bleaching operation, a permanent waving operation or a hair straightening operation or also between the two stages of a permanent waving operation or a hair straightening operation.

When the composition is provided in the form of a conditioner that may optionally be rinsed-out, it may comprise at least one cationic surfactant, for example in a concentration ranging from 0.1 to 10% by weight, relative to the total weight of the composition, for example, from 0.5 to 5% by weight.

According to another embodiment of the present disclosure, the composition can be used as a shampoo.

When the compositions, as disclosed herein, are employed as conventional shampoos, they are applied to wet hair and the foam generated by massage or friction with the hands is subsequently removed, after an optional leave-in time, by rinsing with water or with an aqueous composition, it being possible for the operation to be repeated one or more times.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

The following example serves to illustrate the an embodiment of the present disclosure without, however, exhibiting a limiting nature.

The percentages are expressed as percentage by weight of active material.

EXAMPLES

The following shampoo compositions were prepared:

| As % AM | 1 (invention) | 2 | 3 | 4 | 5 | 6 |
|---|---|---|---|---|---|---|
| Coco glucoside (PLANTACARE 818 UP from Cognis) | 12.5 | 12.5 | 12.5 | 12.5 | | 12.5 |
| Vinylformamide/vinyl-amine (70/30 in moles) copolymer (LUPAMIN 9030 from BASF) | 1 | — | — | | 1 | — |
| Polyvinylformamide (LUPAMIN 9000 from BASF) | — | 1 | | | | — |
| Polyvinylamine (LUPAMIN 9095 from BASF) | | | 1 | | | |
| Polyethyleneimine (LUPASOL P from BASF) | | | | 1 | | |
| Oleth-10 (BRIJ 96 from Uniqema) | | | | | 12.5 | |
| Preservative | q.s. | q.s. | q.s. | q.s. | q.s. | q.s. |
| Fragrance | q.s. | q.s. | q.s. | q.s. | q.s. | q.s. |
| pH agent, q.s. | pH 6.5 | pH 6.5 | pH 6.5 | pH 6.5 | pH 6.5 | pH 6.5 |
| Water, q.s. for | 100 | 100 | 100 | 100 | 100 | 100 |

As disclosed herein, the composition, after application to human hair and the human scalp, may or may not be rinsed out after any treatment. In at least one embodiment, the composition is rinsed out. It can be provided in any form conventionally used in the field concerned, for example in the form of a more or less thickened lotion, of a gel, of a cream, of a spray or of a foam. This composition may be single-phase or multiphase.

Evaluation of the Curl Form Retention 1 gram of each formulation was applied to a lock of natural Caucasian hair with a length (l) of approximately 25 cm weighing 2.7 g.

The locks were massaged, left to stand for 5 minutes and then rinsed out.

The wet locks were subsequently coiled around a curler (Ø=2 cm) and then dried under a hair dryer at 70° C. for 30 minutes.

The curlers were removed and a "ringlet" was obtained, that is to say a lock coiled as a spiral of variable length.

These locks were subsequently suspended from a hook, that is to say subjected to their own weight.

After suspending, the initial length ($l_0$) of the coiled lock was measured.

The locks were subsequently conditioned for 24 hours in a glove box at controlled relative humidity and controlled temperature (25° C./45% Relative Humidity).

After suspending for 24 hours, the length ($l_t$) of the locks which had relaxed under the action of their own weight was again measured.

The % of curl form retention was calculated by the following equation:

$$\% \text{ of form retention} = \left[\frac{(l - l_t)}{(l - l_0)}\right] * 100$$

l: length of the lock before coiling
$l_0$: length of the curled lock immediately after suspending
$l_t$: length of the curled lock after suspending for 24 hours The closer the value obtained is to 100%, the more marked and lasting is the shaping of the lock.

|  | Inventive Ex. 1 | (Ex. 2) | (Ex. 3) | (Ex. 4) | (Ex. 5) | (Ex. 6) |
|---|---|---|---|---|---|---|
| % curl form retention | 75% | 53% | 66% | 61% | 57% | 60% |

The hair treated with the composition of Example 1 exhibited a shaping which was more lasting.

Moreover, the hair treated with the composition of Example 1 exhibited good disentangling and smoothing properties. It was also soft and shiny.

| As g of Active Material | 7 Inventive | 8 | 9 | 10 | 11 |
|---|---|---|---|---|---|
| Coco glucoside (PLANTACARE 818 UP from Cognis) | 11 | 11 | 11 | 11 | 11 |
| Cocoamidopropyl betaine | 2.6 | 2.6 | 2.6 | 2.6 | 2.6 |
| Sodium lauryl ether carboxylate | 1.8 | 1.8 | 1.8 | 1.8 | 1.8 |
| Vinylformamide/vinylamine (70/30 in moles) copolymer (LUPAMIN 9030 from BASF) | 1 | — | — | — | — |
| Polyvinylformamide (LUPAMIN 9000 from BASF) | — | 1 | — | — | — |
| Polyvinylamine (LUPAMIN 9095 from BASF) | — | — | 1 | — | — |
| Polyethyleneimine (LUPASOL P from BASF) | — | — | — | 1 | — |
| Preservative | q.s. | q.s. | q.s. | q.s. | q.s. |
| Fragrance | q.s. | q.s. | q.s. | q.s. | q.s. |
| pH agent q.s. | pH 6.5 | pH 6.5 | pH 6.5 | pH 6.5 | pH 6.5 |
| Water, q.s. for | 100 | 100 | 100 | 100 | 100 |

|  | Inventive (Ex. 7) | (Ex. 8) | (Ex. 9) | (Ex. 10) | (Ex. 11) |
|---|---|---|---|---|---|
| % curl form retention | 78% | 57% | 63% | 52% | 50% |

The hair treated with the composition of Example 7 exhibited a shaping which was more lasting.

Moreover, the hair treated with the composition of Example 7 exhibited good disentangling and smoothing properties. It was also soft and shiny.

Aerosol Compositions According to the Present Disclosure

The following compositions were prepared:

| As g of Active Material | 12 | 13 | 14 |
|---|---|---|---|
| Laureth-5 carboxylic acid | — | 1.8 g | 1.8 g |
| Cocoamidopropyl betaine | — | 2.6 g | 2.6 g |
| Coco glucoside | 12.5 g | 11 g | |
| Polyglyceryl-3 hydroxylauryl ether (CHIMEXANE NF from Chimex) | | | 11 g |
| Vinylformamide/vinylamine (70/30 in moles) copolymer (LUPAMIN 9030 from BASF) | 1 | 1 | 1 |
| Preservative | q.s. | q.s. | q.s. |
| Fragrance | q.s. | q.s. | q.s. |
| pH agent, q.s. | pH 6.5 | pH 6.5 | pH 6.5 |
| Isobutane/propane/butane (PROPEL 45 from Repsol) | 5 g | 5 g | 5 g |
| Water, q.s. for | 100 g | 100 g | 100 g |

What is claimed is:

1. A cosmetic composition comprising, in a cosmetically acceptable aqueous medium:
   at least one non-ionic surfactant chosen from alkylpolyglycosides, and
   at least one vinylformamide/vinylamine copolymer comprising:

from 20 to 40 mol % of units of formula A:

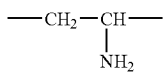

and from 60 to 80 mol % of units of formula B:

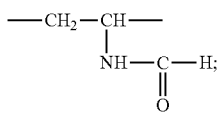

wherein the at least one vinylformamide/vinylamine copolymer consists of units (A) and of units (B).

2. The composition according to claim 1, wherein the at least one non-ionic surfactant is chosen from alkylpolyglycosides of the formula (I):

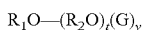

wherein $R_1$ is chosen from linear and branched alkyl and/or alkenyl radicals comprising from 8 to 24 carbon atoms and alkylphenyl radicals, the linear or branched alkyl radical of which comprises from 8 to 24 carbon atoms, $R_2$ is an alkylene radical comprising from 2 to 4 carbon atoms, G is a sugar comprising 5 or 6 carbon atoms, t is a value ranging from 0 to 10 and v is a value ranging from 1 to 15.

3. The composition according to claim 2, wherein $R_1$ is chosen from saturated and unsaturated and linear and branched alkyl radicals comprising from 8 to 18 carbon atoms, t is a value equal to 0, G is chosen from glucose, fructose and galactose, and v is a value ranging from 1 to 4.

4. The composition according to claim 2, wherein G is glucose and v is a value ranging from 1.1 to 2.

5. The composition according to claim 1, wherein the at least one non-ionic surfactant is present in an amount ranging from 0.1 to 40% by weight, relative to the total weight of the composition.

6. The composition according to claim 1, wherein the at least one non-ionic surfactant is present in an amount ranging from 5 to 25% by weight, relative to the total weight of the composition.

7. The composition according to claim 1, wherein the at least one vinylformamide/vinylamine copolymer is present in an amount ranging from 0.01 to 20% by weight, relative to the total weight of the composition.

8. The composition according to claim 1, wherein the at least one vinylformamide/vinylamine copolymer is present in an amount ranging from 0.1 to 5% by weight, relative to the total weight of the composition.

9. The composition according to claim 1, further comprising at least one additional surfactant.

10. The composition according to claim 9, wherein the at least one additional surfactant is present in an amount ranging from 0.1 to 20% by weight, relative to the total weight of the composition.

11. The composition according to claim 1, further comprising at least one additional conditioning agent.

12. The composition according to claim 9, wherein the at least one additional conditioning agent is chosen from poly-α-olefins, fluorinated oils, fluorinated waxes, fluorinated gums, esters of carboxylic acids, silicones, cationic polymers, mineral; oils, vegetable oils, animal oils, ceramides and pseudoceramides.

13. The composition according to claim 9, wherein the at least one additional conditioning agent is chosen from cationic polymers and silicones.

14. The composition according to claim 9, wherein the at last one additional conditioning agent is a silicone.

15. The composition according to claim 9, wherein the at least one additional conditioning agent is a cationic polymer.

16. The composition according to claim 9, wherein the at least one additional conditioning agent is a cationic polymer.

17. The composition according to claim 1, further comprising at least one adjuvant chosen from fatty alcohols comprising 12 to 26 carbon atoms; polymers other than the at least one vinylformamide/vinylamine copolymer; vitamins; fragrances; pearlescent agents; thickeners; gelling agents; trace elements; softeners; sequestering agents; basifying and acidifying agents; preservatives; sunscreens; antioxidants; agents for combating hair loss; antidandruff agents; agents for combating fat; and propellants.

18. The composition according to claim 1, wherein the cosmetically acceptable medium comprises at least one constituent chosen from water, hydrophilic organic solvents, polyols and glycol ethers.

19. The composition according to claim 1, provided in the form of shampoos; gels, hair setting lotions; blow drying lotions; fixing compositions; styling compositions; rinse-out conditioners; leave-in conditioners; permanent waving compositions; hair straightening compositions; dyeing compositions; bleaching compositions; and rinse-out compositions to be applied before or after a dyeing operation, a bleaching operation, a permanent waving operation or a hair straightening operation or between the two stages of a permanent waving operation or of a hair straightening operation.

20. A cosmetic method for cleaning and/or removing makeup from and/or conditioning keratinous substances, comprising:

applying to the keratinous substances, a composition comprising, in a cosmetically acceptable aqueous medium:
at least one non-ionic surfactant chosen from alkylpolyglycosides, and
at least one vinylformamide/vinylamine copolymer comprising:

from 20 to 40 mol % of units of formula A:

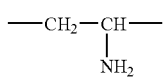

and from 60 to 80 mol % of units of following B:

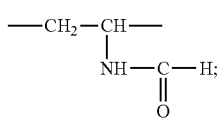

wherein the at least one vinylformamide/vinylamine copolymer consists of units (A) and of units (B).

21. A cosmetic method for treating keratinous substances comprising,
(a) applying to the keratinous substances a composition comprising, in a cosmetically acceptable aqueous medium:
at least one non-ionic surfactant chosen from alkylpolyglycosides and
at least one vinylformamide/vinylamine copolymer comprising:
from 20 to 40 mol % of units of following formula A:

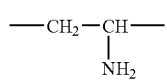

and from 60 to 80 mol % of units of following formula B:

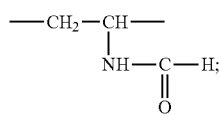

wherein the at least one vinylformamide/vinylamine copolymer consists of units (A) and of units (B); and
(b) optionally rinsing the keratinous substances after an optional leave-in time.

22. A method for washing keratinous substances, comprising:
(a) applying to the keratinous substances a composition comprising, in a cosmetically acceptable aqueous medium:
at least one non-ionic surfactant chosen from alkylpolyglycosides, and
at least one vinylformamide/vinylamine copolymer comprising:
from 20 to 40 mol % of units of following formula A:

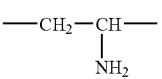

and from 60 to 80 mol % of units of following formula B:

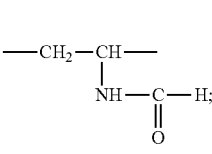

wherein the at least one vinylformamide/vinylamine copolymer consists of units (A) and of units (B); and
(b) optionally rinsing the keratinous substances with water.

* * * * *